United States Patent [19]

Tamm et al.

[11] Patent Number: 5,118,187

[45] Date of Patent: Jun. 2, 1992

[54] FURNACE FOR THE ELECTRO-THERMAL ATOMIZATION OF SAMPLES FOR SPECTROSCOPICAL PURPOSES

[75] Inventors: Rolf Tamm, Salem; Gunther Rodel, Owingen, both of Fed. Rep. of Germany

[73] Assignee: Bodenseewerk Perkin-Elmer GmbH, Uberlingen, Fed. Rep. of Germany

[21] Appl. No.: 556,050

[22] Filed: Jul. 20, 1990

[51] Int. Cl.[5] .......................... G01J 3/30; G01N 21/01
[52] U.S. Cl. ...................................... 356/312; 356/244
[58] Field of Search ................... 356/312, 244

[56] References Cited

U.S. PATENT DOCUMENTS 4,953,977  9/1990  Tomm ........................... 256/312

FOREIGN PATENT DOCUMENTS

| 174728 | 9/1978 | Czechoslovakia | 356/312 |
| 0377253 | 7/1990 | European Pat. Off. | 356/311 |
| 2825759 | 12/1979 | Fed. Rep. of Germany | 356/312 |

*Primary Examiner*—F. L. Evans
*Assistant Examiner*—K. P. Hantis

*Attorney, Agent, or Firm*—Edwin T. Grimes

[57] ABSTRACT

The manufacturing of a furnace for electro-thermal atomization of samples for spectroscopical purposes having a cavity for the accommodation of sample is simplified and improved. To this end, the furnace consists of two halves which are joined along a separating plane intersecting the cavity. The furnace is made of graphite and provided with a layer of pyrolytic graphite. A platform for the accommodation of the sample is integral with one of the halves. A method for the production of such a furnace comprises the method steps: (a) producing two blank parts which engage each other with planar surfaces; (b) machining the two blank parts in common so that a cavity intersected by the plane of the planar surfaces is generated and each of the blank parts forms one half of the furnace; (c) separating the two halves of the furnace which were produced in this way; (d) coating the halves of the furnace separately, the inner surfaces of the cavity forming outer surfaces of each of the two halves of the furnace; and (e) joining the halves of the furnace, generated in this way, to a furnace. There is also a method described for decreasing the refuse in the manufacturing of the furnaces.

21 Claims, 4 Drawing Sheets

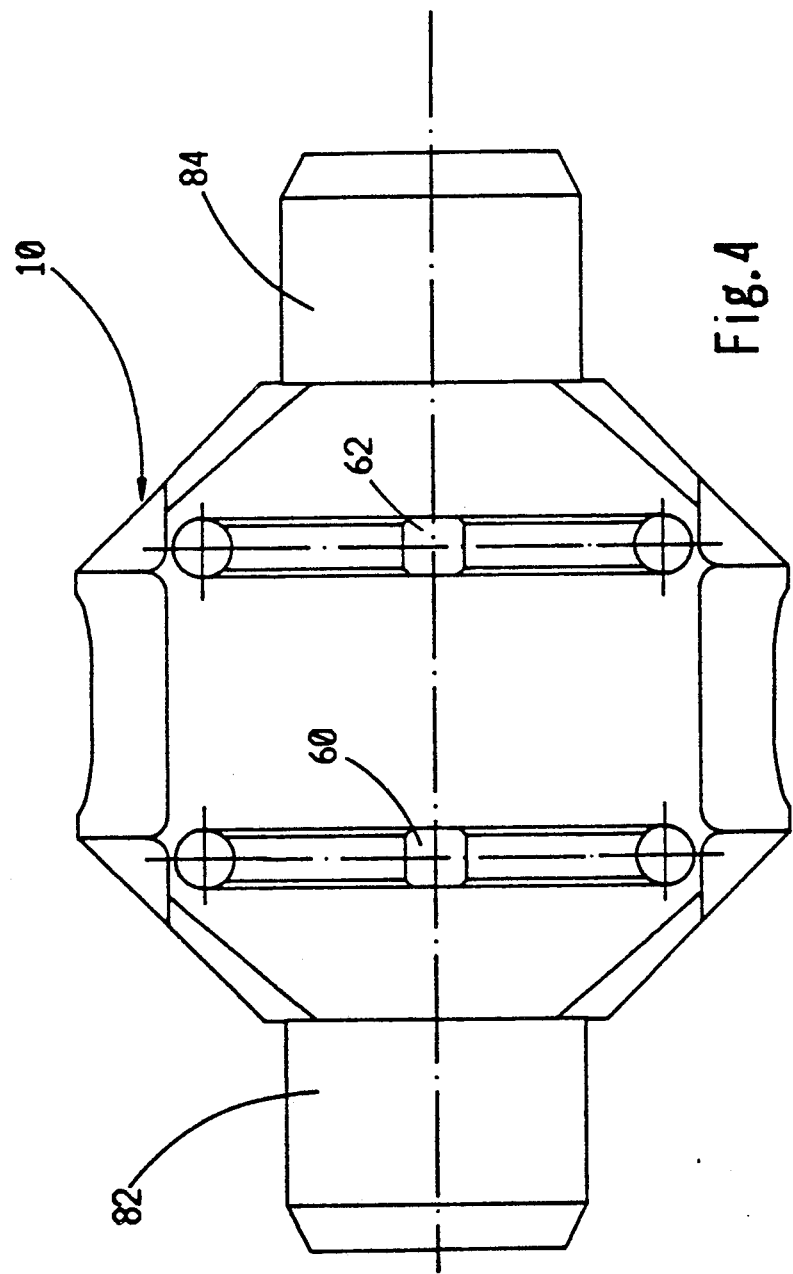

FURNACE FOR THE ELECTRO-THERMAL ATOMIZATION OF SAMPLES FOR SPECTROSCOPICAL PURPOSES

TECHNICAL FIELD

The invention relates to a furnace for the electro-thermal atomization of samples for spectroscopical purposes which has a cavity for the accommodation of the sample.

A very sensitive, quantitative analyzing method for determining the amount of a certain looked for element in a sample is atomic absorption spectroscopy. In atomic absorption spectroscopy, a sample is atomized so that the individual components of the sample are present in their atomic state and form an "atomic vapor". A measuring light beam is passed throughout this atomic vapor. This measuring light beam originates from a line-emitting light source which emits the characteristic resonant lines of the looked for element. Such a measuring light beam is only absorbed by the atoms of the looked for element. Therefore, the absorption of the measuring light beam in the atomic vapor provides a measure of the number of atoms of the looked for element in the path of rays of the measuring light beam, and thus, after suitable calibration, a measure of the concentration of the looked for element in the sample.

For the atomization of the samples, furnaces usually made of graphite are used into which the sample solution is introduced and which are heated by a strong electric current to a high temperature. Thereby, in the interior of the furnace, a "cloud of atoms" is generated throughout which the measuring light beam is passed through aligned openings of the furnace. This is designated as the "electro-thermal atomization".

However, methods are also known wherein in such furnaces, where the sample is electro-thermally heated, a gas discharge is generated whereby the sample atoms are excited to emit characteristic line spectra.

The invention related to a furnace for such spectroscopical purposes and similar spectroscopical purposes.

The invention further relates to a method for producing such a furnace.

BACKGROUND ART

From German patent application 24 20 546, it is known to coat furnaces which are made of a graphite tube with a layer of pyrocarbon in carrying out electro-thermal decomposition of samples. Thereby, in contrast to pure graphite, a non-porous surface is provided by such coating and the sample liquid is prevented from infiltrating the graphite. If such infiltration of sample liquid into the graphite tube were permitted, the atomization of elements of the sample is delayed. Thereby, the sensitivity and the accuracy of the measurement suffer.

Pyrocarbon is a carbon which is generated by thermal decomposition of carburent on the surface of a graphite element, i.e., here a graphite tube. Different methods of supplying a layer of pyrocarbon onto the surface of a graphite tube are known. Such a method is described in German patent application 24 20 546. Other methods work with gaseous carburents such as methane. In vacuo, where the elements which are to be coated are arranged, argon as a carrier gas carries methane over the surfaces which are to be coated, the methane being decomposed there generates the pyrocarbon coating.

In practice, it is often difficult to achieve uniform coating of graphite furnaces with pyrocarbon. This is particularly true for the interior of the cavity into which the sample for the atomization is introduced, i.e., the bore of a graphite tube. The thickness of the layer is difficult to determine. Usually, the thickness of the layer being too small becomes obvious only in practical operation, namely by the early deterioration of the analytical results. The pyrocarbon layer wears out by use, so that, if a layer of pyrocarbon is too small, after relatively few analyses, the sample liquid, as described, will seep away in the material of the furnace which is no longer sufficiently coated.

The "graphite tube atomizer" in which the graphite furnace is formed by a graphite tube through which current flows in its longitudinal direction is described in German patent application 27 18 416.

EP-A2-0 311 761 shows a furnace for the electro-thermal atomization of samples with a tubular furnace body which is provided on opposite sides with longitudinal contact ribs which are, in turn, integral with cylindrical contact pieces. In the bore of the furnace body hollow, generally semi-cylindrical platforms extending through approximately 180° are provided. This platform is integral with the furnace body, i.e., it forms with the furnace body, with the contact ribs, and the contact pieces an integral element made of graphite. Opposite the platform, the furnace body has a sample inlet opening.

It is the purpose of the platform to delay the heating of the sample supplied to the platform to atomization temperature as compared to the heating of the wall of the furnace so that there is already a thermal equilibrium when the sample is finally atomized. This is achieved in that the sample on the platform is heated substantially indirectly by heat radiation from the wall of the furnace.

From German utility model 89 01 529.0. a furnace similar to that described above is known in which the hollow, generally semi-cylindrical platform being integral with the furnace is connected to the furnace body through a narrow web which is arranged on the one side of the platform and only on one side of the longitudinal center plane of the platform.

When the furnaces are produced according to EP-A-0 311 761 or according to German utility model 89 01 529.0, there is relatively much refuse when the integral platform is machined. In addition, very particular problems occur with the coating with pyrocarbon of such furnaces having a complex structure.

DISCLOSURE OF THE INVENTION

It is the object of the invention to design a furnace of the type mentioned above so that it is easy to manufacture.

In particular, the refuse of furnace having an integral platform shall be reduced and the coating with pyrocarbon shall be facilitated.

According to the invention, this object is achieved in that the furnace consists of two halves which are joined along a separating plane intersecting the cavity.

The furnace can be made of graphite and can be provided with a coating, particularly a coating of pyrolytic graphite.

A platform for the accommodation of the sample can be integral with one of the two halves. The furnace can have a tubular furnace portion which on opposite sides is provided with contact pieces extending perpendicular to the axes of the furnace portion and through which an electric current can be circumferentially passed through the furnace portion being in one plane. Then the furnace is separated along this plane comprising the axes. The two halves of the furnace are held together by rings which are slipped onto the contact pieces. Trapezoidal contact ribs are integrally provided between the substantially cylindrical contact pieces and the furnace portion. In the contact ribs around the contact pieces, grooves are provided, into which the cylindrical rings project.

A method for manufacturing a furnace of the type described above comprises the method steps:

(a) producing two blank parts which engage each other with planar surfaces, and (b) machining the two blank parts in common so that a cavity intersected by the plane of the planar surfaces is generated and each of the blank parts forms one half of the furnace, and (c) separating the two halves of the furnace which were produced in this way, (d) coating the halves of the furnace separately, the inner surfaces of the cavity forming outer surfaces of each of the two halves of the furnace, and (e) assembling the halves of the furnace produced in this way, to a furnace.

In this way, the coating of the inner surfaces of the furnace is made while they are freely accessible, i.e., while they form outer surfaces. Thereby, a better and more uniform coating can be achieved.

In order to reduce the refuse of furnaces with an integrated platform, manufacturing can be made in the way that first joined pairs of blank parts are machined such that, in the cavity of the each pair, two hollow, generally cylindrical platforms are formed, one of which is integral with the one half of the furnace, and the other one of which is integral with the other half of the furnace, second joined pairs of blank parts for forming halves of a furnace are machined so that the cavity of each pair forms a continuous bore without any platform being integral therewith. In forming the furnace, each of the halves of a furnace produced from a blank part of the first pairs of blank parts and a half of the furnace produced from a blank part of a second pair of blank parts are joined.

The manufacturing of two halves of a furnace with an integral platform requires the same working steps as the manufacturing of a complete furnace with an integral platform.

When, with the machining of the platform, there is refuse in the blank parts, from which halves of a furnace having an integral platform shall be produced, this refuse normally results only one one half of the furnace. The other half of the furnace can be used and can be combined with an other half of the furnace having no platform. Refuse elements having an integral platform can be reworked to halves of a furnace having no integral platform, if required. According to the statistic refuse rate of the halves of a furnace having an integral platform, the halves of a furnace having no integral platform can be produced in a reduced number.

An embodiment of the invention will now be described in greater detail with reference to the accompanying drawings.

BRIEF DESCRIPTION OF THE DRAWINGS

FIG. 4 is a view of the lower half of the furnace in the direction of the arrow "X" of FIG. 2.

PREFERRED EMBODIMENT OF THE INVENTION

Figure 1:
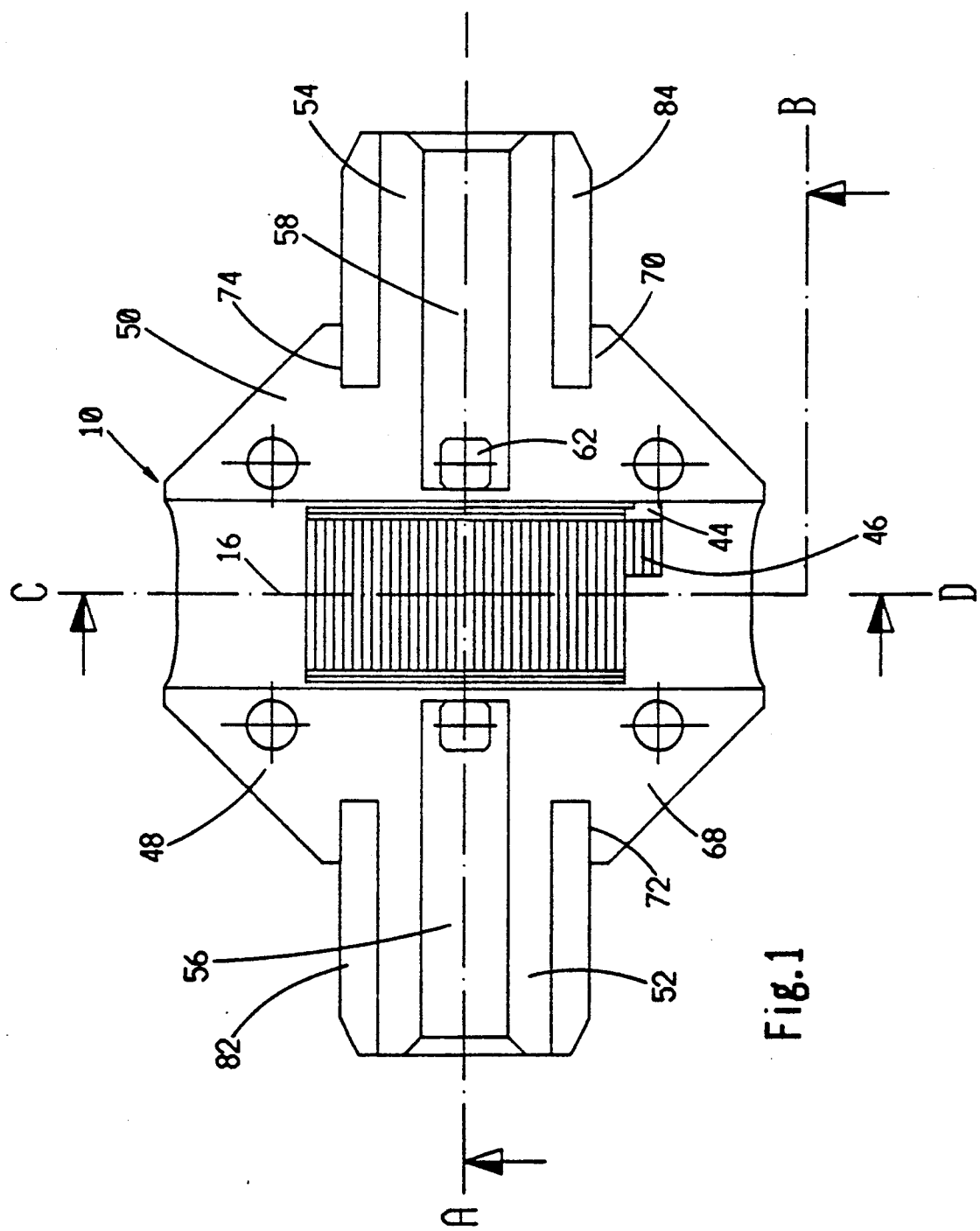
FIG. 1 shows a plan view of a half of a transversely heated furnace having an integral platform.
Figure 2:
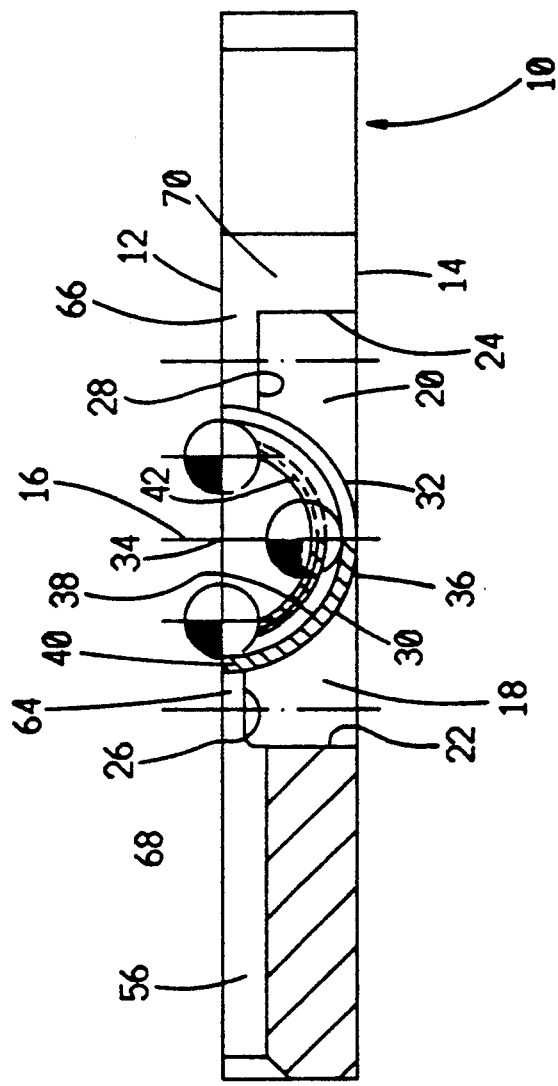
FIG. 2 shows a section taken along the line A-B of FIG. 1.

In FIGS. 1-4, a lower half of a furnace 10 is made of a graphite plate which has an upper planar surface 12 and a lower planar surface 14. On the lower side of the graphite plate, recesses 18 and 20 (FIG. 2) are provided symmetrically to a center plane 16, each of which is limited by a surface 22 and 24, respectively, extending parallel to the planar surface 14 and a convex-cylindrical surface 30 and 32, respectively. The two convex-cylindrical surfaces are matched to form a semi-cylindrical outer surface 36, the axis 34 of which is formed by the intersection of the planar surface 12 and the center plane 16.

On the upper side of the plate, a cylindrical recess 38 is provided coaxially to the outer surface 36. In this way, a half tube 40 is formed which represents half of a tubular furnace body.

A hollow, generally cylindrical platform 42 is concentrically arranged within this half tube 40. The platform 42 is integral with the half tube 40. As can be seen from FIGS. 1 and 3, the platform 42 is only connected to the half tube through a web 44. This web 44 is located on an axial projection 46 at one end of the platform 42 and is connected to the half tube 40 only on one side of the longitudinal center plane 16.

Contact ribs 48 and 50 are provided on both sides adjacent to the half tube 40. In plan view, the contact ribs 48 and 50 are trapezoidal. Contact pieces 52 and 54, respectively, are integral with the contact ribs. The contact pieces are semi-cylindrical. The aligned axes of the cylindrical outer surfaces of the contact pieces are arranged in the planar surface 12 and extend perpendicular to the axis 34 of the half tube 40. Semi-cylindrical, axial grooves 56 and 58, respectively, are also provided in the planar surfaces of the semi-cylindrical contact pieces 52 and 54. The grooves 56 and 58 end in front of the outer surface 36 of the half tube 40 and intersect the recesses 18 and 20, respectively, in passage openings 60 and 62, respectively.

Due to the recesses 18 and 20, the half tube 40 is connected along its edges by relatively thin bridges 64 and 66 to the thicker portions 68 and 70, respectively, of the contact ribs 48 and 50, respectively. The contact pieces 52 and 54 are provided on these thicker portions 68 and 70, the thickness of which corresponds to that of the plate from which the half of the furnace is made. Annular grooves 72 and 74, respectively, are provided in the thicker portions 68 and 70 of the contact ribs 48 and 50 around the contact piece 52.

An "upper" half 76 of the furnace is substantially identical with the described lower half of the furnace 10. However, the upper half 76 has no integral platform 42. The half tube 78 (FIG. 3) has a continuously smooth cylindrical inner surface. The upper half of the furnace 76 has a planar surface 80 corresponding to the planar surface 12.

In order to form a furnace, a lower half of the furnace 10 and an upper half of the furnace 76 are joined with their planar surfaces 12 and 80. Cylindrical rings 82 and 84, respectively, are slipped onto the contact pieces 52 and 54. The cylindrical rings 82 and 84 project into the annular grooves 72 and 74. Thereby, the two halves of the furnace are held in close contact throughout a large portion of their lengths.

Figure 5:
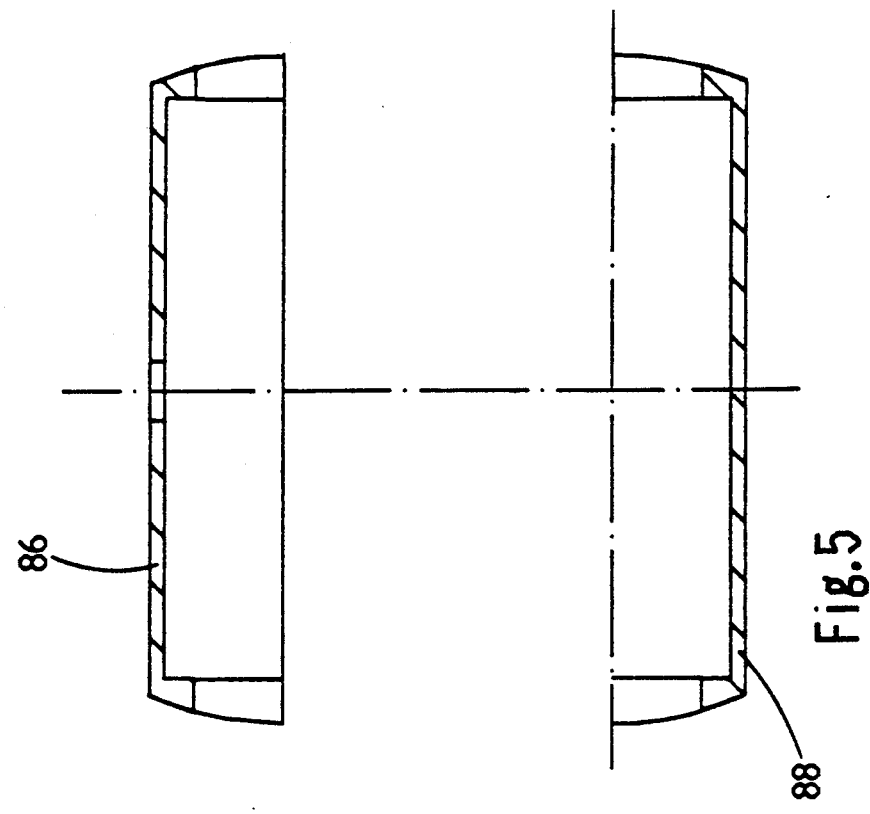
FIG. 5 shows in a section similar to FIG. 3 a furnace having no integral platform.
Figure 3:
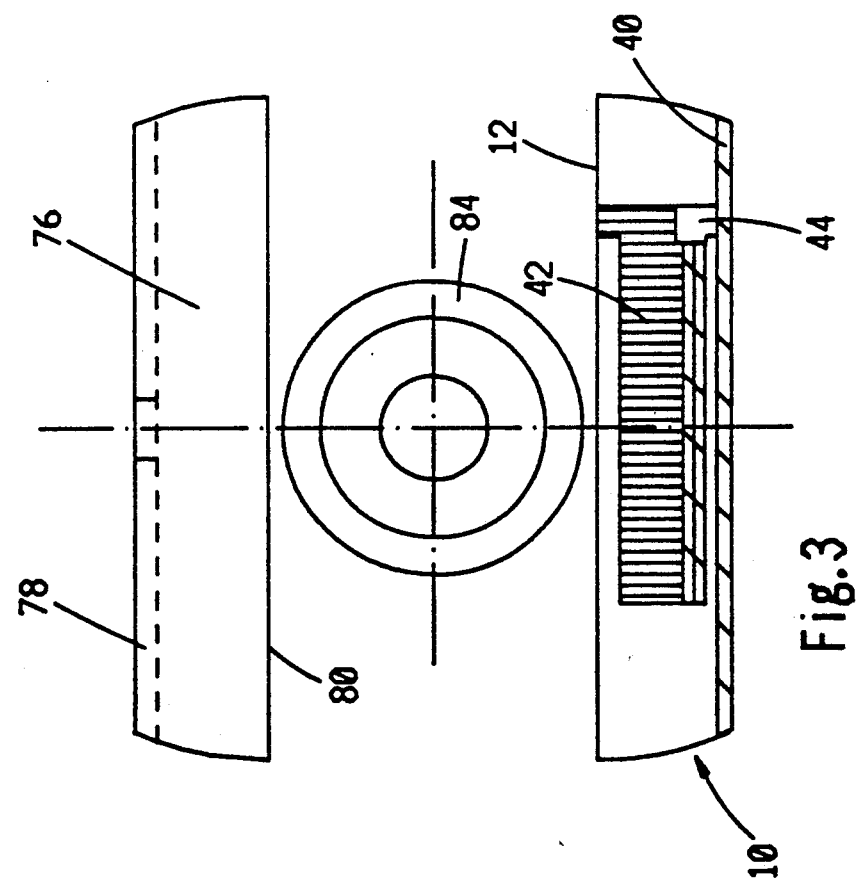
FIG. 3 shows a section taken along the line C-D of FIG. 1, the upper half of the furnace having no integral platform being illustrated together with a ring for the connection of the halves of the furnace.

FIG. 5 shows, in an illustration similar to FIG. 3, a furnace which consists of two identical halves of the furnace 86 and 88 having no platform.

The halves of the furnace are coated with pyrocarbon.

The production of the furnaces is achieved as follows:

Two blank parts having the shape of the mentioned plates with the planar surfaces 12 and 80 are joined and are clamped to each other. Then the plates are machined together. However, in these pairs of plates, either both halves of the furnace or none of the halves of the furnace are provided with integral platforms 40. In practice, the manufacturing of one platform or of two platforms requires the same expenditure.

The halves of the furnaces obtained in this way are separated and coated with pyrocarbon according to a well-known method. The coating of the halves of the furnaces, particularly in the critical areas of the platforms and the inner walls of the bores can, thanks to the separation, be achieved more easily than in the prior art furnaces, since the platforms and the inner walls in the halves of the furnaces represent outer surfaces which are easily accessible and the coating of which presents no difficulties. Each of the "lower" halves of the furnaces 10 having an integral platform 40 and an "upper" half of the furnaces 76 are subsequently joined and are connected to each other by slipping on the rings 82 and 84.

Instead of a connection by the rings 82, 84 also a connection by bonding can be provided. It is also possible that the halves of the furnaces remain separated and in operation are compressed by the contacts having the conical contact surfaces between which the furnace is held in the apparatus. This method can be used particularly in graphite tubes of the prior art type which are held with their end faces between annular contacts and through which current flows longitudinally. Also, such furnaces can advantageously be composed of two halves of a furnace.

We claim:

1. A furnace for the electrothermal atomization of samples for spectroscopical purposes comprising two separate furnace halves which form a cavity, and means for joining said two furnace halves along a separating plane intersecting the cavity, and a platform for the accommodation of a sample, said platform constituting an integral part formed in one piece with one of said two separate furnace halves.

2. A furnace, as set forth in claim 1, wherein the two separate furnace halves are made of graphite and provided with a coating.

3. A furnace, as set forth in claim 2, wherein each of the two separate halves of the furnace is provided with a coating of pyrolytic graphite.

4. A furnace, as set forth in claim 1, wherein: said two separate furnace halves forming said cavity define a tubular furnace portion having cylindrical contacts which extend on opposite sides perpendicular to an axis of the tubular furnace portion and each of which is formed by two semicylindrical contact pieces formed integrally in one piece with respective ones of said two furnace halves, said cylindrical contacts and said tubular furnace portion having respective axes lying in said separating plane along which the two furnace halves are joined.

5. A furnace, as set forth in claim 4, wherein said means for joining said two separate furnace halves contain cylindrical rings which are slipped onto the cylindrical contacts.

6. A furnace, as set forth in claim 5, further including:
a trapezoidal contact rib integrally formed in one piece with and disposed between the semicylindrical contact piece and the furnace half on each one of said opposite sides of each said furnace half,
said trapezoidal contact rib defining a region where the semicylindrical contact piece extends from the trapezoidal contact rib, and a groove in said region; and
a respective one of said cylindrical rings being received in said groove.

7. A method of manufacturing a graphite furnace for electrothermally atomizing a sample for spectroscopic purposes, comprising the steps of:
producing two blank parts which engage each other with planar surfaces, and
conjointly machining the two blank parts and thereby forming in said two blank parts respective graphite furnace halves on opposite sides of the engaged planar surfaces.

8. A method, as set forth in claim 7, further comprising the steps of:
separating the two graphite furnace halves so produced,
applying a pyrolytic graphite coating to the separated graphite furnace halves, such that the two surfaces of the graphite furnace halves form exterior surfaces directly accessible for the pyrolytic graphite coating operation, and
assembling a graphite furnace from the thus obtained pyrolytic graphic coated graphite furnace halves.

9. A method, as set forth in claim 7, wherein:
said step of conjointly machining said two blank parts entails forming, as said two graphite furnace halves in each one of said blank parts, a semicylindrical graphite furnace half, semicylindrical contact pieces and trapezoidal contact ribs extending transversely from opposite sides of said semicylindrical graphite furnace half and being formed integrally in one piece with each other.

10. A method, as set forth in claim 7, wherein said step of conjointly machining said two graphite block blanks includes forming, as said graphite furnace halves, semicylindrical graphite furnace halves in each one of said two blank parts.

11. A method, as set forth in claim 7, wherein said step of conjointly machining said two blank parts includes forming, as said graphite furnace halves in each one of said two blank parts, respective semicylindrical graphite furnace halves each of which has a predetermined axial length and contains a substantially semicylindrical platform extending substantially parallel along at least part of said predetermined axial length of said semicylindrical graphite furnace half and connected thereto by means of a connecting web formed integrally in one piece with said platform and said semicylindrical graphite furnace half.

12. A method, as set forth in claim 11, wherein:
said step of conjointly machining said two blank parts includes forming, as said graphite furnace halves, a first pair of semicylindrical graphite furnace halves in a first pair of said two blank parts;
said step of conjointly machining said two blank parts includes forming, as said graphite furnace halves in each one of a second pair of said blank parts, a second pair of said semicylindrical graphite furnace halves each of which has a predetermined axial length and contains a substantially semicylindrical platform extending substantially parallel along at least part of said predetermined axial length of said semicylindrical graphite furnace half and connected thereto by means of a connecting web formed integrally in one piece with said platform and said semicylindrical graphite furnace half; and
said step of assembling the graphite furnace includes assembling one semicylindrical graphite furnace half of said first pair of semicylindrical graphite furnace halves and one semicylindrical graphite furnace half of said second pair of said semicylindrical graphite furnace halves which contain said substantially semicylindrical, integrally formed platform, in order to form said graphite furnace.

13. A graphite furnace for electrothermally atomizing a sample for spectroscopic purposes, comprising:
two separate furnace halves each of which has opposite sides defining planar surfaces;
said two separate furnace halves contacting each other at respective ones of said planar surfaces which thereby define a separating plane extending between said two separate furnace halves;
each one of said two separate furnace halves containing a semitubular graphite furnace half which is machined into a respective blank part and has a predetermined axial length and is formed integrally in one piece with the separate furnace half; and
said two separate furnace halves being arranged relative to each other such that said semitubular graphite furnace halves are aligned to each other and complement each other along said predetermined axial length with formation of a tubular cavity for receiving a sample.

14. A graphite furnace, as set forth in claim 13, further including a coating applied to said two separate furnace halves.

15. A graphite furnace, as set forth in claim 14, wherein said coating constitutes a pyrolytic graphite coating.

16. A graphite furnace, as set forth in claim 13, further including:
a platform formed integrally in one piece with one of said two separate furnace halves;
said platform extending along at least part of said predetermined axial length of said semitubular graphite furnace half associated with said one separate furnace half and having a shape substantially corresponding to that of said semitubular graphite furnace half; and
said platform being connected to said semitubular graphite furnace half by means of a connecting web formed integrally in one piece with said platform and said semitubular graphite furnace half at a predetermined location of said semitubular graphite furnace half.

17. A graphite furnace, as set forth in claim 13, further including:
a plural number of contact pieces for supplying electrical current to said graphite furnace;
each one of said two separate furnace halves containing two of said plural number of contact pieces;
said two contact pieces being machined into said separate furnace half, being formed integrally in one piece with the separate furnace half and the respective semitubular graphite furnace half and extending from opposite sides of said semitubular graphite furnace half substantially transverse to said predetermined axial length of said semitubular graphite furnace half;
said plural number of contact pieces being aligned and complementing each other with formation of two contacts of a predetermined external shape on opposite sides of the graphite furnace;
said contacts and said tubular cavity formed by said two graphite furnace halves, defining respective axes; and
said axes respectively defined by said contacts and said tubular cavity extending in said separating plane between said two separate furnace halves.

18. A graphite furnace, as set forth in claim 17, wherein said semitubular graphite furnace halves constitute semicylindrical graphite furnace halves, said plural number of contact pieces constitute semicylindrical contact pieces and said two contacts constitute cylindrical contacts.

19. A graphite furnace, as set forth in claim 18, further including:
a plural number of trapezoidal contact ribs integrally formed in one piece with said two separate furnace halves and said semicylindrical graphite furnace halves and disposed on said opposite sides of said semicylindrical graphite furnace halves; and
each one of said trapezoidal contact ribs interconnecting a respective one of said plural number of semicylindrical contact pieces and a respective one of said semicylindrical graphite furnace half.

20. A graphite furnace, as set forth in claim 19, further including:
a plural number of retaining rings adapted in shape to the predetermined external shape of said two contacts;
said plural number of retaining rings surrounding respective ones of said two contacts on one of said opposite sides of said graphite furnace.

21. A graphite furnace, as set forth in claim 20, wherein each one of said trapezoidal contact ribs contains a groove which surrounds said respective semicylindrical contact piece at a predetermined spacing for receiving said a respective one of said plural number of retaining rings.

* * * * *